(12) United States Patent
Poliwoda et al.

(10) Patent No.: US 12,400,377 B2
(45) Date of Patent: Aug. 26, 2025

(54) COMPUTER-IMPLEMENTED METHOD FOR DETERMINING AT LEAST ONE GEOMETRIC PARAMETER REQUIRED FOR EVALUATING MEASUREMENT DATA

(71) Applicant: Volume Graphics GmbH, Heidelberg (DE)

(72) Inventors: Christoph Poliwoda, Heidelberg (DE); Soren Schüller, Heidelberg (DE); Matthias Flessner, Heidelberg (DE); Thomas Günther, Heidelberg (DE)

(73) Assignee: VOLUME GRAPHICS GMBH, Heidelberg (DE)

( * ) Notice: Subject to any disclaimer, the term of this patent is extended or adjusted under 35 U.S.C. 154(b) by 929 days.

(21) Appl. No.: 17/512,613

(22) Filed: Oct. 27, 2021

(65) Prior Publication Data

US 2022/0130081 A1 Apr. 28, 2022

(30) Foreign Application Priority Data

Oct. 28, 2020 (DE) ...................... 10 2020 128 288.5

(51) Int. Cl.
*G06T 11/00* (2006.01)
*G01T 7/00* (2006.01)

(52) U.S. Cl.
CPC ............ *G06T 11/005* (2013.01); *G01T 7/005* (2013.01)

(58) Field of Classification Search
CPC ....... G06T 11/005; G06T 15/00; G06T 17/00; G06T 2207/10072; G06T 2207/10076;
(Continued)

(56) References Cited

U.S. PATENT DOCUMENTS 5,550,376 A 8/1996 Gupta
6,379,043 B1 * 4/2002 Zylka ................... G01N 23/044
378/207
(Continued)

FOREIGN PATENT DOCUMENTS

DE  10 2006 011 008 A1  2/2007
DE  10 2008 035 656 A1  3/2010
(Continued)

OTHER PUBLICATIONS

German Patent and Trademark Office, First Examination Report for German Application No. 10 2020 128 288.5, mail date Apr. 27, 2021, 4 pages.
(Continued)

*Primary Examiner* — Manav Seth
(74) *Attorney, Agent, or Firm* — SoCal IP Law Group LLP; Angelo Gaz (57) ABSTRACT

The invention relates to a computer-implemented method for determining at least one geometric parameter required for an evaluation of measurement data, wherein the measurement data are determined by means of a radiographic measurement of a component having a component geometry, wherein a digital component representation is generated by the measurement data, wherein the method comprises the following steps: determining the measurement data by means of a radiographic measurement of a component; identifying regions one of in the digital component representation or in the component geometry as reference regions; determining at least one geometric parameter required for an evaluation of the determined measurement data, by means of the reference regions. Less computing power than in the prior art is required with the method. Furthermore, the method is able to be employed without great complexity.

19 Claims, 1 Drawing Sheet

(58) Field of Classification Search
CPC . G06T 2207/10081; G06T 2207/10124; G01T 7/005
See application file for complete search history.

(56) References Cited

U.S. PATENT DOCUMENTS

| | | | | | |
|---|---|---|---|---|---|
| 7,844,094 | B2* | 11/2010 | Jeung | ................... | G01T 1/2985 |
| | | | | | 382/154 |
| 7,950,849 | B2* | 5/2011 | Claus | ................... | A61B 6/583 |
| | | | | | 378/207 |
| 9,036,887 | B2* | 5/2015 | Fouras | ................. | A61B 6/4085 |
| | | | | | 382/132 |
| 12,226,233 | B2* | 2/2025 | Chen | ...................... | G06N 20/00 |
| 2003/0167142 | A1* | 9/2003 | Chell | .................... | G01S 7/5205 |
| | | | | | 702/107 |
| 2007/0122020 | A1* | 5/2007 | Claus | ................... | G06T 11/005 |
| | | | | | 382/131 |
| 2007/0147580 | A1* | 6/2007 | Wu | ........................ | A61B 6/583 |
| | | | | | 378/18 |
| 2017/0164919 | A1* | 6/2017 | Lavallee | .............. | A61B 6/4405 |
| 2025/0045984 | A1* | 2/2025 | Zhang | ................... | G01N 23/10 |

FOREIGN PATENT DOCUMENTS

| | | |
|---|---|---|
| DE | 102009049818 A1 | 4/2011 |
| DE | 102015225130 A1 | 6/2017 |
| DE | 102017201164 B3 | 1/2018 |
| DE | 102016214062 A1 | 2/2018 |
| DE | 102017205113 A | 9/2018 |

OTHER PUBLICATIONS

European Patent Office, Extended European Search Report for EP Application No. 21203209.8, mail date Mar. 21, 2022.
European Patent Office, Office Action for EP Application No. 21203209.8, mail date Jul. 12, 2023.

* cited by examiner

COMPUTER-IMPLEMENTED METHOD FOR DETERMINING AT LEAST ONE GEOMETRIC PARAMETER REQUIRED FOR EVALUATING MEASUREMENT DATA

RELATED APPLICATION INFORMATION

This patent claims priority from German Patent Application No. DE 10 2020 128 288.5, filed Oct. 28, 2020, all of which are incorporated herein by reference in their entirety.

BACKGROUND

Field

The invention relates to a computer-implemented method for determining at least one geometric parameter required for an evaluation of measurement data.

Description of the Related Art

The interior of objects or living organisms can be represented by means of radiographs, such as e.g. the images of a measurement effected by computed tomography. In order to be able to carry out e.g. a measurement effected by computed tomography, it is necessary to know the geometric calibration resulting from the geometric positioning and orientation of the radiation source, the detector and the object to be measured with respect to one another for each individual recorded radiograph. In an individual radiograph, the geometric positioning and orientation of the radiation source, the detector and the component with respect to one another, in particular the pose of the x-ray source and the detector relative to the component or rotary table, can be referred to as recording geometry. The geometry calibration is required by the reconstruction in which volume data of the object are determined from a multiplicity of radiographs with different recording geometries of an object. Errors of the geometric calibration cause image aberrations in the reconstructed volume data, e.g. unsharp edges, double edges or distortions, etc., and hence measurement errors when carrying out dimensional measurements or other analyses such as a defect analysis.

A geometric calibration requires knowledge of the geometric parameters of the apparatus for carrying out the radiographic measurement on the object. In the general case, nine parameters or degrees of freedom, also called DoF, are required for each individual radiograph. These are three translational and three rotational parameters in relation to the detector and three translational parameters in relation to the radiation source if the rigid object to be measured is chosen as reference. Other definitions are likewise possible, however. In this way, it is possible to establish an assignment of pixels of radiographs, which correspond to two-dimensional projections, to coordinates in space or voxels of three-dimensional volume data. This general case, e.g. for complex trajectories of robotic computed tomography apparatuses, requires a determination of the parameters for each radiograph. In this case, local parameters are determined for each radiograph.

For specific trajectories, e.g. the circular trajectory in axial computed tomography or for spiral computed tomography, there may be fewer parameters. Global parameters are determined in this case, and it is possible to calculate the local parameters for each individual radiograph from said global parameters on the basis of the predefinitions of the trajectory. This does not preclude registering deviations from an ideal recording geometry for the global parameters for each individual radiograph, said deviations already being taken into account directly in the local parameters.

However, in particular robotic computed tomography apparatuses and C-arm computed tomography apparatuses generally cannot position the detector and the radiation source accurately. This concerns not only systematic deviations, but also random deviations, such that the deviations from an ideal recording geometry can thus be different for each measurement. Even normal axial computed tomography apparatuses have not just the systematic deviations but also random deviations, e.g. as a result of thermal effects, wobble of the axis of rotation, slow drifts of the spot in the radiation source or the axes, pitting of the tube, vibrations, deviations or errors of the axes. Furthermore, movements of the object to be measured or of the living organism during the radiographic measurement may be a cause.

U.S. Pat. No. 7,186,023 B discloses radiographing a dedicated standard, beforehand or subsequently in all required recording geometries. This may be referred to as so-called offline calibration. The recording geometry can be deduced in each case on the basis of the position of the standard in the individual radiographs. However, the accuracy of the calibration decreases over time since the apparatuses for carrying out the radiographic measurement, in particular robotic computed tomography apparatuses, are not perfectly stable. This calibration or this calibrating process should therefore be repeated regularly. This is time-consuming. Moreover, it can happen that drift effects occur even during a measurement, directly after the calibration. In the case of flexible or adaptive trajectories, moreover, it is often not possible to carry out a calibration beforehand, since the trajectory to be used is not yet known.

Furthermore, it is known to derive a calibration from the measurement data themselves. This may be referred to as online calibration. In the case of an online calibration, the uncertainty of transferring an offline calibration to the time of the measurement no longer applies. However, these calibrations are inherently less accurate as a rule, since a dedicated standard with a known geometry cannot be used. Furthermore, these procedures are computationally intensive and complex.

It is therefore an object of the invention to provide a computer-implemented method which requires less computing power than the prior art and is able to be employed without great complexity.

SUMMARY

Main features of the invention are specified herein.

In a first aspect, the invention relates to a computer-implemented method for determining at least one geometric parameter required for an evaluation of measurement data, wherein the measurement data are determined by means of a radiographic measurement of a component having a component geometry, wherein a digital component representation is generated by the measurement data, wherein the method comprises the following steps: determining the measurement data by means of a radiographic measurement of a component; identifying regions in the digital component representation and/or in the component geometry as reference regions; determining at least one geometric parameter required for an evaluation of the determined measurement data, by means of the reference regions.

The invention involves carrying out an online calibration in which highly accurate geometric parameters are determined. To that end, at least one reference region is identified in the digital component representation generated from a reconstruction of the measurement data or the radiographs. A reference region comprises only a portion of the component, and not the entire component. A geometric parameter required for the evaluation of the determined measurement data, i.e. e.g. for a dimensional measurement, is determined merely on the basis of said at least one reference region. For this purpose, in the component geometry, i.e. in the radiographs or the volume data of the reconstruction or the segmentation thereof, regions or geometries in or on the component are determined which are suitable as well as possible for being used to carry out a geometric calibration. Ideally, the calibration is then calculated as in the case of a measurement of a dedicated standard, without the scan of such a standard being required. This reduces the complexity of the calibration. Furthermore, less computing power than in known online calibration methods is required. In a targeted manner suitable reference regions are sought which are taken as a basis for implementing the calibration or determining the geometric parameters. The targeted use of said reference regions reduces the required computation time, in particular per iteration, or possibly enables higher accuracies in comparison with known online calibration methods.

If a known geometric calibration is assumed, the method can for example furthermore be used to determine parameters of other geometric effects and to correct these effects in this way. These effects may be deviations of the detector from the nominal shape and a non-rigid behaviour, i.e. deformations, of the object or component to be measured during the measurement.

In one example, parameters of two out of three geometric effects may be known and the parameters of the third geometric effect can be determined. It is likewise conceivable for the parameters of two or even all three geometric effects to be determined simultaneously.

The term reference regions denotes selected geometries of the measurement object or selected partial regions of the digital component representation, in particular of the volume data, which have the same geometry. In one example, the reference regions can also be identified with the aid of available prior knowledge about the component geometry. Reference regions can also be determined already before carrying out the measurement.

Furthermore, it is possible for example to determine the reference regions in the radiographs or the measurement data, e.g. regions with high contrast and/or sharp edges. The regions of the radiographs are used in which the reference regions, i.e. the geometries of the component or the selected partial regions of the volume data of the digital component representation, are imaged. In this case, it may be conceivable, for example, to carry this out individually for each projection.

The evaluation of the determined measurement data can include a reconstruction, in particular.

The geometric parameters required for the evaluation can be for example parameters that describe the recording geometry, the deviations of the detector from the nominal shape or the non-rigid behaviour of the component during the measurement.

In accordance with one example, the at least one geometric parameter can describe a recording geometry used for the radiographic measurement of the component.

This can be referred to as geometric calibration of an apparatus for carrying out the radiographic measurement, in particular of a computed tomography system. One possibility for the parameterization is the description of each radiograph of the measurement data by nine parameters or degrees of freedom.

Furthermore, for example, between step: determining the measurement data, and step: identifying regions in the digital component representation and/or in the component geometry as reference regions, the method can comprise the following step: determining a provisional reconstruction of the component as digital component representation from at least one portion of the determined measurement data by means of at least one predefined geometric start parameter, wherein in step: identifying regions in the digital component representation and/or in the component geometry as reference regions, the regions are identified in the digital component representation and/or in a segmentation based on the digital component representation.

The reference regions can be identified with the aid of a provisional reconstruction or digital component representation or a segmentation carried out on said provisional reconstruction, wherein the provisional reconstruction is carried out on the basis of at least one portion of the radiographs or the measurement data. This can mean, for example, that the determination of the measurement data has not yet been concluded, but the measurement data already present or a portion of the measurement data present are used for a provisional reconstruction.

In this case, after step: determining at least one geometric parameter, the method can for example furthermore comprise the following steps: repeating the following steps as long as a predefined termination criterion is not satisfied: determining a further provisional reconstruction of the component as digital component representation from at least one portion of the determined measurement data by means of the at least one geometric parameter; identifying regions in the digital component representation as reference regions; determining at least one further geometric parameter that replaces the at least one geometric parameter and is required for an evaluation of the measurement data, by means of the reference regions.

Since the geometric parameters are now more accurate than before the repetitions, the new provisional digital component representation or reconstruction has a higher quality. The at least one reference geometry can thus be better selected. Furthermore, better knowledge about the reference regions is known, e.g. the relative positioning of reference regions or of the geometries contained therein with respect to one another, which is utilized in the new iteration. The repetition step can be terminated if e.g. a defined number of iterations has been reached, the geometric parameters no longer change significantly between iteration steps, i.e. they converge, or the measurement data or the volume data reconstructed from them satisfy a defined quality measure.

In accordance with a further example, step: determining at least one geometric parameter can comprise at least one of the following substeps: determining the positions of the reference regions with respect to one another in the digital component representation, determining projected positions of the reference regions in at least one portion of the determined measurement data, and using the positions of the reference regions and the projected positions of the reference regions for determining at least one geometric parameter; and/or simulating a radiographic measurement on the digital component representation and/or a segmentation based on the digital component representation, wherein the simulation generates simulated measurement data, and using a comparison of the reference regions in the determined measurement data and the simulated measurement data for determining at least one geometric parameter; and/or varying at least one geometric parameter of the digital component representation in at least one projection of the digital component representation, determining at least one quality parameter of a reconstruction of the component that uses the at least one projection, repeating the processes of varying the at least one geometric parameter and determining at least one quality parameter until at least one optimized geometric parameter has a quality parameter that is a maximum value of all determined quality parameters, and using the at least one optimized geometric parameter as determined at least one geometric parameter.

When determining the reference regions, it is possible for example to determine for which of the three substeps for determining the geometric parameters these can be used in each case. Small, spherical inclusions are advantageous, in principle, for example for all three substeps explained above. Irregularly shaped inclusions are advantageous for the last two substeps explained above. Regions of a material transition with high contrast are advantageous for the last substep: varying at least one geometric parameter of the digital component representation in at least one projection of the digital component representation, determining at least one quality parameter of a reconstruction of the component that uses the at least one projection, repeating the processes of varying the at least one geometric parameter and determining at least one quality parameter until at least one optimized geometric parameter has a quality parameter that is a maximum value of all determined quality parameters, and using the at least one optimized geometric parameter as determined at least one geometric parameter.

In one example of the substep: determining the positions of the reference regions with respect to one another in the digital component representation, determining projected positions of the reference regions in at least one portion of the determined measurement data, and using the positions of the reference regions and the projected positions of the reference regions for determining at least one geometric parameter, it is possible, apart from a global translation and rotation that together constitute 6° of freedom, then to determine the positions of the reference regions with respect to one another and thus also the distances with respect to one another. The positions of the reference regions can thus be described in a dedicated coordinate system. This information can be used to determine the geometric parameters for which the projected positions of the reference regions and the positions thereof in the provisional digital component representation are, preferably as far as possible, consistent. In the case of the geometric calibration, the projected positions are thus taken as a basis for determining the respective pose, i.e. the position and orientation of detector and position of x-ray source in relation to the reference regions and thus the defined coordinate system. This geometric information can then be used for a correct reconstruction of a digital component representation, which can replace the provisional digital component representation.

For this example it is advantageous to use as reference regions geometries of the component whose projected positions are readily recognizable or localizable in the radiographs. One example thereof is spherical geometries. On account of the degrees of freedom, possibly of each individual radiograph, a certain minimum number of geometries is necessary in this case. Furthermore, it is advantageous to use three, four or even more reference regions in order to achieve an accurate geometric calibration. Furthermore, for example, a comparatively large number of reference regions, e.g. at least 8, 20, 50 or 100, can be used. It is then unproblematic if the projected positions of the individual reference regions can be localised comparatively inaccurately in the radiographs, mutually overlap in part or are not visible in all the radiographs, since this can be compensated for again by way of the improved statistics.

Furthermore, in a further example, it is not possible to take account of reference regions in individual projections if these mutually overlap one another in the radiographs or at least are very close to one another or are situated in a region of the projection in which the measurement values, greyscale values in the case of computed tomography, or the background of the measurement values, e.g. a greyscale value background, are comparatively inhomogeneous. This makes it more difficult to determine the accurate position of the reference geometry in the projection.

In general, non-linear equations have to be solved in order to determine the geometric parameters. An iterative solution with the aid of the Levenberg-Marquardt algorithm is conceivable, for example. However, the determined solution may land at a local minimum.

For an axial recording geometry, for example, an ellipse fit of the path of a reference geometry in the radiographs may be more stable provided that free trajectories are not used.

In order to carry out a complete geometric calibration, the substep: determining at least one geometric parameter can comprise at least one of the following substeps: determining the positions of the reference regions with respect to one another in the digital component representation, determining projected positions of the reference regions in at least one portion of the determined measurement data, and using the positions of the reference regions and the projected positions of the reference regions for determining at least one geometric parameter, can be carried out for all the radiographs.

In substep: simulating a radiographic measurement on the digital component representation and/or a segmentation based on the digital component representation, wherein the simulation generates simulated measurement data, and using a comparison of the reference regions in the determined measurement data and the simulated measurement data for determining at least one geometric parameter, it is possible for example to search for that set of geometric parameters for the radiograph under consideration for which the simulated radiograph of the simulated measurement data and the actually measured radiographs of the determined measurement data for the reference regions have the best correspondence. Similarity measures can be used for this purpose, e.g. a correlation of pixel greyscale values in the case of computed tomography. It is conceivable, for example, to compare a gradient representation in each case. The simulated radiograph can be carried out e.g. with the aid of methods based on ray casting or forward projections. In order to carry out a complete geometric calibration, this substep can be carried out for all the radiographs.

Furthermore, corresponding reference regions which enable a projection-based correction are determined. However, instead of "analytically" matching the position of the reference geometry in 3D with the projected position in 2D as in the substep: determining at least one geometric parameter, comprising at least one of the following substeps: determining the positions of the reference regions with respect to one another in the digital component representation, determining projected positions of the reference regions in at least one portion of the determined measurement data, and using the positions of the reference regions and the projected positions of the reference regions for determining at least one geometric parameter, the sub step of simulating a radiographic measurement on the digital component representation and/or a segmentation based on the digital component representation, wherein the simulation generates simulated measurement data, and using a comparison of the reference regions in the determined measurement data and the simulated measurement data for determining at least one geometric parameter, works on the image data. The digital radiographing is compared with the actually measured radiograph and the geometric parameters which bring about a maximum correspondence are sought. This is carried out only on the regions of the determined, e.g. distinctive, reference regions. This significantly reduces the computation time.

In accordance with one example of the substep: varying at least one geometric parameter of the digital component representation in at least one projection of the digital component representation, determining at least one quality parameter in at least one reference region of a reconstruction of the component that uses the at least one projection, repeating the processes of varying the at least one geometric parameter and determining at least one quality parameter in at least one reference region until at least one optimized geometric parameter has a quality parameter that is a maximum value of all determined quality parameters, and using the at least one optimized geometric parameter as determined at least one geometric parameter, the set of geometric parameters for the at least one radiograph under consideration is sought for which the volume data of the reference regions have the best properties. These properties may be, e.g., contrast, entropy, resolution or sharpness of edges/material transitions, since erroneous geometric parameters usually have a negative effect on these properties. This can be assessed in each case on the basis of the volume data themselves and/or on the basis of a greyscale value histogram. An optimization can additionally be carried out to the effect that peaks of the individual materials that are separated as well as possible stand out in the greyscale value histogram.

In one example concomitantly for a geometric calibration, an individual projection or radiograph has only a weak effect on the volume data. Therefore, it is advantageous to optimize the geometric parameters of all the projections jointly, i.e. the global parameters, since otherwise there would be very many degrees of freedom.

For the further optimization of the quality of the volume data, the regions of the volume which is evaluated for this are selected intelligently. These regions are the reference regions. In this way, the optimization can be carried out more rapidly and more purposely and thus possibly also more accurately.

All three substeps described above are suitable, in principle, for determining the geometric parameters of the three geometric effects mentioned above. Here, too, the geometric calibration is the most important effect in practice. In this case, for example, a plurality of the substeps described above can be combined or used simultaneously. Some of the reference regions can be used for example just for one of the substeps, and others for two or three of the substeps described above, depending on suitability.

The substep: determining the positions of the reference regions with respect to one another in the digital component representation, determining projected positions of the reference regions in at least one portion of the determined measurement data, and using the positions of the reference regions and the projected positions of the reference regions for determining at least one geometric parameter, tends to be better suited if the reference regions used are simple structures clearly recognizable in the projections, such as e.g. spheres or small inclusions, which can be localized exactly. The substep: simulating a radiographic measurement on the digital component representation and/or a segmentation based on the digital component representation, wherein the simulation generates simulated measurement data, and using a comparison of the reference regions in the determined measurement data and the simulated measurement data for determining at least one geometric parameter, tends to be better suited if more complex structures are used as reference regions.

In one example of geometric calibration, the first two substeps mentioned are best suited or tend to be best suited to robotic computed tomography apparatuses or free trajectories, likewise in order to determine the deviations of the individual projections from the associated ideal trajectory. All three substeps are suitable, in principle, for determining the global parameters in conventional axial computed tomography or helical computed tomography.

In this case, for example, in substep: determining the positions of the reference regions with respect to one another in the digital component representation, determining projected positions of the reference regions in at least one portion of the determined measurement data, and using the positions of the reference regions and the projected positions of the reference regions for determining at least one geometric parameter; geometries of the reference regions can be taken into account when determining the projected positions.

Taking account of the geometries of the reference regions concerns, in particular, a deviation from a spherical geometry. In this regard, e.g. knowledge about the three-dimensional geometry of the reference region, e.g. from a defect analysis, can be used in order to predict corresponding parameters, e.g. a centroid of an extremum of the values of the pixels of a radiograph or a border of the imaging of the reference region, in the two-dimensional projection. These can thereupon be identifiable better or exactly. The accuracy of the assignment of the positions of the geometries in the radiographs or of the projections among one another or to the position in the digital component representation is increased in this way. This can be implemented for example by determining the principle axes of a geometry and thereby determining or modelling the effects on the projection.

Furthermore, for example, in substep: simulating a radiographic measurement on the digital component representation and/or the segmentation based on the digital component representation, wherein the simulation generates simulated measurement data, and using a comparison of the reference regions in the determined measurement data and the simulated measurement data for determining at least one geometric parameter; the simulated measurement data can be generated only for regions in the digital component representation which have reference regions.

In other words, the simulated radiographies are calculated only in the regions of the reference regions and possibly a small area surrounding the reference regions and are compared with the determined radiographs from the measurement data. The required computing power is thus reduced. The derivative or gradient representation or other representations, e.g. following the application of a Sobel operator, of the projections can be considered or compared here, for example. Furthermore, the radiographic measurement can be simulated only for a conical region of the component, the conical region including the reference region. Simulated measurement data are then generated only for the regions of the component in which geometric parameters are required for the evaluation. This further reduces the required computing power.

In another example, in substep: varying at least one geometric parameter of the digital component representation in at least one projection of the digital component representation, determining at least one quality parameter in at least one reference region of a reconstruction of the component that uses the at least one projection, repeating the processes of varying the at least one geometric parameter and determining at least one quality parameter in the at least one reference region until at least one optimized geometric parameter has a quality parameter that is a maximum value of all determined quality parameters, and using the at least one optimized geometric parameter as determined at least one geometric parameter; only the regions of the digital component representation which have reference regions can be reconstructed and analysed by means of the varied geometric parameters in the digital component representation.

As a result of the repeated processes of varying the geometric parameters and reconstructing and analysing when determining the optimized geometric parameter, the correct geometric parameters can be identified. Since only small regions have to be reconstructed, this proceeds more rapidly or more iterations are possible at the same time.

The step: identifying regions in the digital component representation and/or in the component geometry as reference regions can comprise for example the following substep: segmenting interfaces of the digital component representation.

In this example, the segmentation can comprise both outer interfaces and inner interfaces. Inner interfaces can be inner surfaces of the component or in the component, e.g. can be those of inclusions, pores or defects, which can be very small. Advantageously, in one example, the segmentation can be carried out with sub-voxel accuracy. The segmentation can furthermore be carried out for example on the basis of the volume data of the digital component representation, but likewise on the basis of the measurement data or the radiographs. Furthermore, it is conceivable, for example, to consider both the segmentation and the volume data jointly for the identification of the reference regions. In this case, for example, it is possible to use small spherical geometries with high absorption and/or good contrast in the volume data of the digital component representation.

Furthermore, for example, in step: identifying regions in the digital component representation and/or in the component geometry as reference regions, regions in which material and/or air inclusions are arranged can be identified.

As a rule, the material and/or air inclusions are not known in advance and are only identified with the aid of a suitable analysis of the measurement data or of the volume data of the digital component representation. This can be for example an analysis that determines a defect mask. Advantageously, it is possible to use only material inclusions, for example, since these have a better contrast than air inclusions. This applies in particular to metal inclusions. In particular, this feature is advantageous in combination with the substep: determining the positions of the reference regions with respect to one another in the digital component representation, determining projected positions of the reference regions in at least one portion of the determined measurement data, and using the positions of the reference regions and the projected positions of the reference regions for determining at least one geometric parameter.

In accordance with a further example, in step: identifying regions in the digital component representation and/or in the component geometry as reference regions, regions can be identified which have a geometry which is spherical or is classified as spherical taking account of a predefined tolerance range.

This can be advantageous particularly with regard to material and/or air inclusions since the inclusions have spherical geometries, which can easily be localized in projections or radiographs. Furthermore, they are imaged very similarly in the projections in different radiographing directions. An analysis of the geometry of the material and/or air inclusions is necessary in order to identify those having the corresponding geometry. This can be done on the basis of a defect mask, for example, which can be obtained from a defect analysis, for example. In additive manufacturing, in particular, there may be many material inclusions. In order to determine the position of spherical geometries in the projections, with maximum sub-pixel accuracy, it is possible to determine for example the mass centroid of the imaging of the geometry in the projection. In particular, this feature is advantageous in combination with the substep: determining the positions of the reference regions with respect to one another in the digital component representation, determining projected positions of the reference regions in at least one portion of the determined measurement data, and using the positions of the reference regions and the projected positions of the reference regions for determining at least one geometric parameter.

Furthermore, in step: identifying regions in the digital component representation and/or in the component geometry as reference regions, for example regions can be identified which are an object of an assembly in the component and have an absorption coefficient which is arranged within a predefined interval.

These may be for example screws, nails, bolts, rivets, metal balls, cables or parts of a plug. Small objects of assemblies are preferably selected. It is advantageous if the absorption coefficients of these objects are comparatively high. In particular, this feature is advantageous in combination with the substep: determining the positions of the reference regions with respect to one another in the digital component representation, determining projected positions of the reference regions in at least one portion of the determined measurement data, and using the positions of the reference regions and the projected positions of the reference regions for determining at least one geometric parameter.

Furthermore, in step: identifying regions in the digital component representation and/or in the component geometry as reference regions, for example regions can be identified which are arranged in a volume of the component geometry in which no reference regions or a number of reference regions which is less than a predefined limit value were identified.

The achievable accuracy of the geometric calibration can be increased in this way since e.g. some errors of the geometric calibration are manifested differently in different regions of the measurement volume having the component. Particularly in combination with the substep: determining the positions of the reference regions with respect to one another in the digital component representation, determining projected positions of the reference regions in at least one portion of the determined measurement data, and using the positions of the reference regions and the projected positions of the reference regions for determining at least one geometric parameter, more stable results are obtained if the geometries are arranged in a manner distributed as much as possible or as far away from one another as possible.

By way of example, in step: determining at least one geometric parameter required for an evaluation of the measurement data, by means of the reference regions, certainty parameters of the reference regions can be taken into account.

The certainty parameter can indicate the level of certainty of a position of the reference region assigned to it. Reference regions that have been assessed as uncertain on the basis of their certainty parameter can for example be given a lower weighting e.g. in the case of a weighted adaptation. The risk of an erroneous adaptation is minimized in this way.

In all the examples mentioned above, it is possible to choose reference regions having surfaces which are oriented in all spatial directions. This ensures that e.g. in computed tomography radiographs, greyscale value transitions can be present in all spatial directions and be analysed. Examples of geometries for which this is particularly advantageous are: a sphere, e.g. in the case of an inclusion, a hemisphere, e.g. in the case of a pore, or virtually any completely closed geometry without edges. This is particularly advantageous in combination with the substep: varying at least one geometric parameter of the digital component representation in at least one projection of the digital component representation, determining at least one quality parameter of a reconstruction of the component that uses the at least one projection, repeating the processes of varying the at least one geometric parameter and determining at least one quality parameter until at least one optimized geometric parameter has a quality parameter that is a maximum value of all determined quality parameters, and using the at least one optimized geometric parameter as determined at least one geometric parameter.

Furthermore, when determining the geometric parameters, it is possible to take into account for example further prior knowledge about the positioning of the components: x-ray source, detector and component to be measured with respect to one another. This can be taken into account in another example for individual projections or radiographs. In this regard, for example, it may be known that at the beginning and at the end of a measurement x-ray source and detector are situated in known, "locked" or calibrated positions that are known with great accuracy, while the uncertainty of the positioning is greater in other projections.

Carrying out the determination of the geometric parameters can also be influenced by prior knowledge about the geometry if for example standard geometries such as threads or standardized surfaces are represented in the measurement data for which, in some cases, without further reference measurement, it can be assumed that these have been manufactured correctly. This knowledge, e.g. about the pitch of the thread or that the standardized surface has a very good flatness, can have an influence such that geometric parameters are identified for which these predefinitions are also fulfilled in the measurement data. In this way, for example, a determination of additional geometric parameters can be carried out, e.g. the geometric magnification or voxel size. Generally, e.g. dimensions or geometries derived from a CAD model of the component can be used for this purpose. In this case, it is possible to create or predefine a catalogue of standard geometries that are sought in the measurement data. This step is particularly advantageous if dimensions or geometries are used which are typically manufactured exactly.

In accordance with a further example, geometries from a central plane of the digital component representation can be selected or the measurement data on which the geometries are based can be provided with a lower level of uncertainty or a corresponding certainty parameter, since cone beam artefacts have the least effect here.

The data about the reference regions can originate for example from a further source, e.g. from another measurement of the same component. In this case, it may be advantageous if internal structures are imaged. Examples of this are a high-quality or high-resolution measurement by computed tomography or micrographs.

If a CAD model, a provisional reconstruction or other information about the geometry of the component is present, in accordance with a further example it is possible to calculate simulated projections over the entire angle space of the possible radiographing directions, optionally with a certain "density". The available real projections or radiographs of the determined measurement data can be compared with these simulated projections and the best correspondence can be identified. A coarse recording geometry can be determined by way of this assignment. This example is particularly advantageous if the prior knowledge concerning the geometric calibration is quite inaccurate. In a further example, if necessary, further relevant simulated projections can additionally be subsequently calculated in a targeted manner if locally the "density" of the radiographing directions is not sufficient for the determination of the recording geometry.

When carrying out the method according to the invention, in another example using a measurement by computed tomography, it is possible to take account of the fact that there is a spectrum-dependent penetration depth of the photons into the detector. Components of different materials can thus be imaged with different effective magnifications in the case of a cone beam geometry, which causes measurement errors. Taking this effect into account can minimize these measurement errors.

If geometries are identified in the projections, in a further example it may be advantageous to identify them separately for each projection.

If the component has been or is produced by means of additive manufacturing, it may be advantageous for example to position suitable geometries, e.g. small spherical structures, within the object in order that these can be used for the method according to the invention.

In a further aspect, the invention relates to a computer program product comprising instructions which are executable on a computer and which, when executed on a computer, cause the computer to carry out the method according to the preceding description.

Advantages and effects and also developments of the computer program product are evident from the advantages and effects and also developments of the method described above. In this regard, therefore, reference is made to the preceding description.

DESCRIPTION OF THE DRAWINGS

Further features, details and advantages of the invention are evident from the wording of the following description of exemplary embodiments with reference to the drawings, in which.

DETAILED DESCRIPTION

Figure 1:
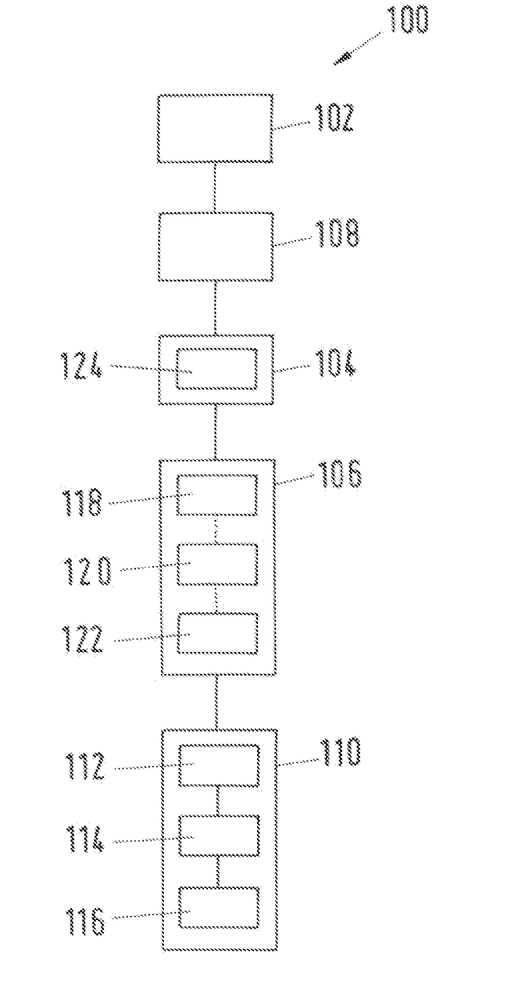
FIG. 1 shows a flow diagram of the computer-implemented method for determining at least one geometric parameter required for an evaluation of measurement data.

The computer-implemented method for determining at least one geometric parameter required for an evaluation of measurement data is designated hereinafter by the reference sign 100 in accordance with FIG. 1.

The method 100 determines geometric parameters used to evaluate measurement data from a radiographic measurement of a component. The at least one geometric parameter can describe e.g. a recording geometry used for the radiographic measurement of the component.

In a first step 102, the measurement data are determined by means of a radiographic measurement. In this case, the measurement data can e.g. be obtained from a measurement by computed tomography and be projections or radiographs of the component having a component geometry. The component geometry describes the real three-dimensional shape of the component. A digital component representation can be generated from the measurement data, e.g. by way of a reconstruction of the volume data of the component from the projections.

In an optional step 108, at least from a portion of the determined measurement data a provisional reconstruction can be carried out in order to obtain provisional volume data. Furthermore, a provisional digital component representation is thereby obtained. The provisional reconstruction is carried out by means of at least one predefined geometric start parameter. The predefined geometric start parameter can be predefined by a user or an alternative method or can be an estimated or empirical value which was determined from earlier uses of the method 100 as at that time a final geometric parameter for identical or similar components.

Afterwards, a step 104 involves identifying at least one reference region in the digital component representation or in the component geometry, e.g. regions in which material and/or air inclusions are arranged, and/or regions having a geometry which is spherical or is classified as spherical taking account of a predefined tolerance range. Furthermore, e.g. regions can be identified which are an object of an assembly in the component and have an absorption coefficient which is arranged within a predefined interval, or which are arranged in a volume of the component geometry in which no reference regions or a number of reference regions which is less than a predefined limit value were identified. In this case, the at least one reference region comprises only a portion of the digital component representation or of the component geometry.

Step 104 can comprise the optional substep 124 of segmenting interfaces in the digital component representation.

If step 108 was carried out, the identification of the reference region can be carried out in the digital component representation that was obtained by means of the provisional reconstruction. Alternatively or additionally, the identification can be carried out in a segmentation of the digital component representation.

Reference regions and their positions are determined on the basis of a measurement in which the previous errors or inaccuracies of the geometric parameters relevant to the reconstruction still have an effect. Consequently, these errors could in part be reflected in the reference regions or in the position thereof and therefore not be identifiable or correctable in the projections. In order to reconstruct a volume region, data from different regions of the detector are used, such that local deviations can average out. The reconstruction of the volume data taken as a basis for determining the reference regions therefore has a compensating effect on the errors. These errors therefore tend to have little effect on the reference regions or the position thereof. Analogously, the step of segmentation or surface determination can also have a compensating effect. On the basis of the information of the reference regions, these errors can be determined and corrected in the next reconstruction.

If an unknown lateral offset of the detector by a few pixels is present, for example, this does not cause systematic distortions of the volume data to a first approximation in axial computed tomography. Merely an unsharpness within an x-y-plane of the detector is caused. The (centroid) positions of the reference regions, e.g. defects, remain uninfluenced by this, such that the reference region is "correct" and can be used for a correction.

Reference regions can be identified e.g. by means of a CAD model of the component. The CAD model is one example of prior knowledge about the component to be measured. The component geometry defined in the CAD model is then used to select appropriate regions of the component which are suitable as reference regions in order thereby to obtain geometric parameters for the evaluation of the measurement data. These may be e.g. regions which can be imaged with certainty and with high quality in the radiographic measurement. These may be e.g. regions which are expected to be clearly visible in the measurement data on account of their geometry or their material composition.

Alternatively or additionally, the regions can be selected from the digital component representation or the segmentation thereof, without prior knowledge being used. To that end, e.g. in the radiographs, firstly regions with high contrast and/or sharp edges can be selected as reference regions. For this purpose, the radiographs can be evaluated individually for appropriate regions. From these regions the regions which are imaged in the digital component representation and/or the segmentation thereof are selected.

Identifying regions in the digital component representation can mean, for example, that reference regions which are particularly well suited to the geometric calibration are sought without special prior knowledge about the geometry of the component. Furthermore, the identifying can be, for example, determining the position of known or defined reference regions of the component in the measurement data.

In step 106, at least one geometric parameter for the evaluation of the measurement data is determined by means of the reference regions. For example, a certainty parameter of the reference regions can be taken into account in this case. The evaluation can be e.g. a final reconstruction, i.e. the generation of volume data from the measurement data. Alternatively, the evaluation can be a measurement of geometries directly in the projection data, the geometric assignment of the projections to one another being taken into account.

The geometric parameters can describe for example the recording geometry, the deviations of the detector from the nominal shape or a non-rigid behaviour, e.g. deformations, of the component during the measurement.

Deviations of the detector from the nominal shape can be e.g. deformations of the detector, in particular in robotic computed tomography. Furthermore, the deviations can result from structural tolerances of the detector if e.g. pixel spacings have certain deviations.

The optional substeps 118, 120 and 122 of step 106 describe hereinafter method steps for determining at least one geometric parameter which are optionally combinable with one another.

In substep 118, for this purpose it is possible to determine the positions of the reference regions with respect to one another in the digital component representation. This can encompass both the uncertainty of the determination or localization of the geometry in three dimensions and the uncertainty with which a geometry in a two-dimensional projection can be recognized or its position and/or orientation can be determined. Furthermore, this substep involves determining projected positions of the reference regions in at least one portion of the determined measurement data and using them in order to determine the at least one geometric parameter.

Optionally, in substep 118, it is possible to take account of geometries of the reference regions when determining the projected positions.

With substep 120, it is possible to simulate a radiographic measurement on the digital component representation and/or a segmentation based on the digital component representation. The simulation generates simulated measurement data in which the reference regions are likewise imaged. The reference regions of the simulated measurement data are compared with the reference regions of the determined measurement data. Regions of the volume data and/or measurement data or projections which have e.g. increased noise are taken into account to a lesser extent in the assessment of the correspondence of simulated and determined measurement data since the information content of these regions is lower. The result of the comparison is used to determine the at least one geometric parameter.

Optionally, in substep 120, the simulated measurement data can be generated only for regions in the digital component representation which have reference regions.

Furthermore, with substep 122, it is possible to vary at least one geometric parameter of the digital component representation in at least one projection or radiograph of the digital component representation. A reconstruction of the component which is based at least one the at least one projection is carried out with the at least one varied geometric parameter. At least one quality parameter in at least one reference region is determined for this reconstruction. The processes of varying the at least one geometric parameter and determining the at least one quality parameter in the at least one reference region are repeated until at least one optimized geometric parameter has a quality parameter which is a maximum value of all the determined quality parameters. In this case, varying the at least one geometric parameter creates a varied reconstruction, the quality of which is assessed once again. Regions of the volume data and/or measurement data or projections which have e.g. an increased noise are taken into account to a lesser extent in the assessment of the quality of the volume data since the information content of these regions is lower. If an optimized geometric parameter was determined in accordance with the termination criterion mentioned above, this parameter is used as the at least one geometric parameter for the evaluation of the measurement data.

Optionally, in substep 122, only the regions of the digital component representation which have reference regions can be newly reconstructed and analysed by means of the varied geometric parameters in the digital component representation.

Information about, optionally local, deviations of the detector from the nominal shape, i.e. an ideal detector geometry, can be derived with the aid of the reference regions, particularly if very many high-quality reference regions are present and the geometric calibration is known.

A real detector is not perfect since the spacing between the pixels is generally not constant; moreover, deformations perpendicular to the detector area can occur. There are thus deviations of the detector from a perfect pixel matrix. These deviations, virtually three degrees of freedom per pixel, are to a first approximation constant over many measurements. However, they can also vary between different projections, e.g. in the case of a detector which is positioned by a robot arm and becomes deformed differently in different orientations under its own weight or as a result of thermal effects. These deviations can be described for example by a pixel-by-pixel definition of the deviation of the respective pixel from the nominal position. These deviations from an ideal detector geometry cannot usually be identified on the basis of an analysis of a projection as long as the radiographed or imaged geometry is not known. By virtue of the fact that the reference regions and their positions with respect to one another are known, certain, optionally local, deviations can be determined with the aid of the projections, such that they can thereupon be corrected or taken into account in the reconstruction. There may also be a z-component, e.g. if the detector is bent. The distortions can be dependent on the temperature and thus different for each projection. Nevertheless, the largest proportions are usually constant over the projections. Advantageously, global distortions, e.g. in the form of deviation vectors, are then determined for each pixel.

In order to reduce the number of degrees of freedom, it may be advantageous to determine the deviation vectors only for a portion of the pixels and to interpolate between them.

The reference regions are used to determine geometric parameters concerning a non-rigid behaviour, e.g. deformations, of the component during the measurement or for each projection, particularly if very many high-quality reference regions are present and the geometric calibration is known.

Without correction the measurement data are inconsistent in the case of a deformation of the measured component. This is manifested in image aberrations in the volume data. The non-rigid behaviour can be corrected or taken into account in the reconstruction, such that a consistent volume that is as free from errors as possible can be reconstructed.

The non-rigid behaviour of the component can be represented e.g. by an array of displacement vectors. Various resolutions of the array and, resulting therefrom, a correspondingly varying total number of support points are possible here. Since the number of degrees of freedom is comparatively large as also in the case of the deviations of the detector from the nominal shape, comparatively many reference regions are required for a determination of the geometric parameters.

Application examples are e.g. thin-walled components, which become deformed under their own weight during the measurement, or deformations triggered by thermal effects, e.g. heating of the component in delimited regions.

Advantageously, at least a coarse estimation of the geometric parameters sought is initially present. However, it is sufficient if the coarse recording geometry is known only for individual projections, since this is sufficient e.g. for a provisional reconstruction. Furthermore, a first coarse estimation of the parameters can be carried out with other methods, for example using consistency conditions with regard to line integrals in different projections or the so-called epipolar consistency conditions, whereupon the accurate determination is carried out with the aid of the invention.

The invention is preferably used in the case of measurements which use an area detector.

For an exact localization of recognized geometries of the component, it is possible to use in each case a clearly defined position of the geometry, e.g. the mass centroid or a point of intersection of edges such as the corner of a cube.

With further method steps, it is furthermore possible to determine the two angles of the detector tilting which are arranged "out-of-plane", i.e. the two directions which do not have the detector normal as axis of rotation. It is thus possible to carry out the determination of the geometric magnification or voxel size, the out-of-plane tiltings of the detector, and/or further geometric parameters. To that end, for example, the relative positioning of detector, x-ray source and axis of rotation can be determined with the aid of sensors, e.g. by means of a laser interferometer.

In another example, during the measurement, a further object of known geometry, e.g. two spheres at a known distance from one another, can be situated in the measurement region. In a further example, knowledge about certain geometries of the component can be used, for example if a reference measurement over a portion of the geometries of the component is present, in order to transfer this knowledge to the entire measurement.

In accordance with one example for the application of a geometric calibration of an axial computed tomography apparatus or a spiral computed tomography apparatus, firstly the global parameters can be determined. Thus, firstly the number of degrees of freedom is expediently restricted. This is used as a start value or starting point for a determination of the local geometric parameters or the deviations of the individual projections from the ideal trajectory in the axial computed tomography apparatus or spiral computed tomography apparatus.

After step 106, the method can comprise the optional step 110. In step 110, optional substeps 112, 114 and 116 are repeated as long as a predefined termination criterion is not satisfied.

Substep 112 involves determining a further provisional reconstruction of the component as digital component representation. At least one portion of the determined measurement data is used for this purpose. In this case, the determination of the measurement data need not necessarily have been concluded and can continue to be carried out in parallel. In this case, the already available measurement data or a portion of the available measurement data can form the at least one portion of the determined measurement data. Alternatively, after the end of the determination of the measurement data, a portion of the already available measurement data can be used for the provisional reconstruction. The reconstruction is carried out by means of the geometric parameter determined in step 106.

Afterwards, in substep 114, once again regions in the digital component representation are identified as reference regions. Since the digital component representation was determined by means of the geometric parameter, the digital component representation used in substep 114 tends to be more accurate than that in step 104. That is to say that the reference regions determined in substep 114 also tend to have a better quality than those determined in step 104.

In substep 116, at least one further geometric parameter that replaces the previous at least one geometric parameter is determined by means of the reference regions from substep 114. Owing to the reference regions tending to be better, the at least one further geometric parameter tends to be more accurate than the geometric parameter determined in step 106.

In the repetition of substeps 112 to 116, the at least one further geometric parameter determined in substep 114 is treated as the at least one geometric parameter.

The predefined termination criterion can comprise e.g. the condition that the difference between the newly determined at least one geometric parameter and the previous geometric parameter lies below a predefined threshold value and thus the newly determined at least one geometric parameter does not constitute a significant improvement over the previous at least one geometric parameter.

The order of the steps described in this example can be varied in any desired way, in so far as is reasonably implementable.

The computer-implemented method 100 can be carried out by means of a computer program product on a computer. In this case, the computer program product comprises instructions which are executable on a computer. When these instructions are executed on a computer, they cause the computer to carry out the method.

The invention is not restricted to any of the embodiments described above, but rather is modifiable in diverse ways. All features and advantages that emerge from the description and the drawing, including structural details, spatial arrangements and method steps, may be essential to the invention both by themselves and in a wide variety of combinations.

It is claimed:

1. A computer-implemented method for determining at least one geometric parameter required for an evaluation of measurement data, wherein the measurement data are determined by means of a radiographic measurement of a component having a component geometry, wherein a digital component representation is generated by the measurement data, wherein the method comprises the following steps:
    determining the measurement data by means of a radiographic measurement of a component;
    identifying regions one of in the digital component representation or in the component geometry as reference regions; and
    determining at least one geometric parameter required for an evaluation of the determined measurement data, by means of the reference regions;
    wherein determining the at least one geometric parameter includes at least the following substep:
        determining the positions of the reference regions with respect to one another in the digital component representation, determining projected positions of the reference regions in at least one portion of the determined measurement data, and using the positions of the reference regions and the projected positions of the reference regions for determining at least one geometric parameter.

2. The method according to claim 1, wherein between step: determining the measurement data, and step: identifying regions one of in the digital component representation or in the component geometry as reference regions, the method comprises the following step:
    determining a provisional reconstruction of the component as digital component representation from at least one portion of the determined measurement data by means of at least one predefined geometric start parameter,
    wherein in step: identifying regions one of in the digital component representation or in the component geometry as reference regions, the regions are identified one of in the digital component representation or in a segmentation based on the digital component representation.

3. The method according to claim 2, wherein after step: determining at least one geometric parameter, the method furthermore comprises the following steps:
    repeating the following steps as long as a predefined termination criterion is not satisfied:
        determining a further provisional reconstruction of the component as digital component representation from at least one portion of the determined measurement data by means of the at least one geometric parameter;

identifying regions in the digital component representation as reference regions; and determining at least one further geometric parameter that replaces the at least one geometric parameter and is required for an evaluation of the measurement data, by means of the reference regions.

4. The method according to claim 1, wherein in substep: determining the positions of the reference regions with respect to one another in the digital component representation, determining projected positions of the reference regions in at least one portion of the determined measurement data, and using the positions of the reference regions and the projected positions of the reference regions for determining at least one geometric parameter; geometries of the reference regions are taken into account when determining the projected positions.

5. The method according to claim 1, wherein in step: identifying regions in one of the digital component representation or in the component geometry as reference regions, regions in which one of material or air inclusions are arranged are identified.

6. The method according to claim 1, wherein in step: determining at least one geometric parameter required for an evaluation of the measurement data, by means of the reference regions, certainty parameters of the reference regions are taken into account.

7. A non-transitory computer program product comprising instructions which are executable on a computer and which, when executed on the computer, cause the computer to carry out the method according claim 1.

8. A computer-implemented method for determining at least one geometric parameter required for an evaluation of measurement data, wherein the measurement data are determined by means of a radiographic measurement of a component having a component geometry, wherein a digital component representation is generated by the measurement data, wherein the method comprises the following steps:

determining the measurement data by means of a radiographic measurement of a component;

identifying regions one of in the digital component representation or in the component geometry as reference regions; and determining at least one geometric parameter required for an evaluation of the determined measurement data, by means of the reference regions;

wherein determining the at least one geometric parameter includes at least the following substep:

simulating a radiographic measurement on one of the digital component representation or a segmentation based on the digital component representation, wherein the simulation generates simulated measurement data, and using a comparison of the reference regions in the determined measurement data and the simulated measurement data for determining at least one geometric parameter.

9. The method according to claim 8, wherein between step: determining the measurement data, and step: identifying regions one of in the digital component representation or in the component geometry as reference regions, the method comprises the following step:

determining a provisional reconstruction of the component as digital component representation from at least one portion of the determined measurement data by means of at least one predefined geometric start parameter, wherein in step: identifying regions one of in the digital component representation or in the component geometry as reference regions, the regions are identified one of in the digital component representation or in a segmentation based on the digital component representation.

10. The method according to claim 9, wherein after step: determining at least one geometric parameter, the method furthermore comprises the following steps:

repeating the following steps as long as a predefined termination criterion is not satisfied:

determining a further provisional reconstruction of the component as digital component representation from at least one portion of the determined measurement data by means of the at least one geometric parameter;

identifying regions in the digital component representation as reference regions; and determining at least one further geometric parameter that replaces the at least one geometric parameter and is required for an evaluation of the measurement data, by means of the reference regions.

11. The method according to claim 8, wherein in substep: simulating a radiographic measurement on one of the digital component representation or the segmentation based on the digital component representation, wherein the simulation generates simulated measurement data, and using a comparison of the reference regions in the determined measurement data and the simulated measurement data for determining at least one geometric parameter; the simulated measurement data are generated only for regions in the digital component representation which have reference regions.

12. The method according to claim 8, wherein in step: identifying regions in one of the digital component representation or in the component geometry as reference regions, regions in which one of material or air inclusions are arranged are identified.

13. A non-transitory computer program product comprising instructions which are executable on a computer and which, when executed on the computer, cause the computer to carry out the method according claim 8.

14. A computer-implemented method for determining at least one geometric parameter required for an evaluation of measurement data, wherein the measurement data are determined by means of a radiographic measurement of a component having a component geometry, wherein a digital component representation is generated by the measurement data, wherein the method comprises the following steps:

determining the measurement data by means of a radiographic measurement of a component;

identifying regions one of in the digital component representation or in the component geometry as reference regions; and determining at least one geometric parameter required for an evaluation of the determined measurement data, by means of the reference regions;

wherein determining the at least one geometric parameter includes at least the following substep:

varying at least one geometric parameter of the digital component representation in at least one projection of the digital component representation, determining at least one quality parameter in at least one reference region of a reconstruction of the component that uses the at least one projection, repeating the processes of varying the at least one geometric parameter and determining at least one quality parameter in at least one reference region until at least one optimized geometric parameter has a quality parameter that is a maximum value of all determined quality parameters, and using the at least one optimized geometric parameter as determined at least one geometric parameter.

15. The method according to claim 14, wherein between step: determining the measurement data, and step: identifying regions one of in the digital component representation or in the component geometry as reference regions, the method comprises the following step:
determining a provisional reconstruction of the component as digital component representation from at least one portion of the determined measurement data by means of at least one predefined geometric start parameter,
wherein in step: identifying regions one of in the digital component representation or in the component geometry as reference regions, the regions are identified one of in the digital component representation or in a segmentation based on the digital component representation.

16. The method according to claim 15, wherein after step: determining at least one geometric parameter, the method furthermore comprises the following steps:
repeating the following steps as long as a predefined termination criterion is not satisfied:
determining a further provisional reconstruction of the component as digital component representation from at least one portion of the determined measurement data by means of the at least one geometric parameter;
identifying regions in the digital component representation as reference regions; and
determining at least one further geometric parameter that replaces the at least one geometric parameter and is required for an evaluation of the measurement data, by means of the reference regions.

17. The method according to claim 14, wherein in substep: varying at least one geometric parameter of the digital component representation in at least one projection of the digital component representation, determining at least one quality parameter in at least one reference region of a reconstruction of the component that uses the at least one projection, repeating the processes of varying the at least one geometric parameter and determining at least one quality parameter in at least one reference region until at least one optimized geometric parameter has a quality parameter that is a maximum value of all determined quality parameters, and using the at least one optimized geometric parameter as determined at least one geometric parameter; only the regions of the digital component representation which have reference regions are reconstructed and analysed by means of the varied geometric parameters in the digital component representation.

18. The method according to claim 14, wherein in step: identifying regions in one of the digital component representation or in the component geometry as reference regions, regions in which one of material or air inclusions are arranged are identified.

19. A non-transitory computer program product comprising instructions which are executable on a computer and which, when executed on the computer, cause the computer to carry out the method according claim 14.

* * * * *